US00PP12409P2

(12) United States Plant Patent
Zaiger et al.

(10) Patent No.: US PP12,409 P2
(45) Date of Patent: Feb. 12, 2002

(54) INTERSPECIFIC TREE NAMED: 'DAPPLE FIRE'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/816,195

(22) Filed: Mar. 26, 2001

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct interspecific tree [(Plum×Plum nectarine)×(Peach×Plum peach)]; the characteristics of the tree and its fruit are with the tree budded on Citation Rootstock (U.S. Plant Pat. No. 5,112), and grown on Hanford sandy loam soil with Storie Index rating 95, in USDA Zone 9, near Modesto, Calif., using standard commercial cultural fruit growing practices such as pruning, thinning, spraying, irrigation and fertilization. Its novelty consists of the following combination of desirable features:

1. Heavy and regular production of fruit.
2. Vigorous and upright growth.
3. Fruit with very good flavor and eating quality.
4. Fruit with a high degree of attractive brownish red skin color.
5. Fruit having firm flesh with good handling and shipping quality.

1 Drawing Sheet

BACKGROUND OF THE VARIETY

FIELD OF THE INVENTION

In the field of plant genetics we conduct an extensive and continuing plant breeding program including the origination and asexual reproduction of orchard trees, and of which interspecifics, plums, peaches, nectarines, apricots and cherries are exemplary. It is against this background of our activities that the present variety of interspecific tree was originated and asexually reproduced by us in our experimental orchard located near Modesto, Stanislaus County, Calif.

PRIOR VARIETIES

Among the existing varieties of interspecific, plum and peach trees, which are known to us, and mentioned herein, are Interspecific Tree Dapple Dandy (U.S. Plant Pat. No. 9,554), the Plum Tree Red Beaut (U.S. Plant Pat. No. 2,539), the Peach Tree O'Henry (U.S. Plant Pat. No. 2,964) and the Interspecific Tree Citation (U.S. Plant Pat. No. 5,112).

ORIGIN OF THE VARIETY

The new and distinct variety of interspecific Prunus tree [(*Prunus salicina*×(*Prunus salicina*×*Prunus persica* var. *nucipersica*))×(*Prunus persica*×(*Prunus salicina*×*Prunus persica*))] was developed by us in our experimental orchard as a first generation cross between two selected seedlings with the field identification numbers 150LB5 and 14GD84. (These non-patented selections were developed and selected by us for future use in our breeding program). The maternal parent 150LB5 originated from a cross of a plum seedling of unknown parentage with a seedling of an open pollinated Red Beaut Plum (U.S. Plant Pat. No. 2,539) crossed with a nectarine of unknown parentage. The paternal parent (14GD84) originated from a peach seedling selection of open pollinated O'Henry Peach (U.S. Plant Pat. No. 2,964) seeds crossed with a selected seedling originating from a cross of Red Beaut Plum (U.S. Plant Pat. No. 2,539) with a peach of unknown parentage. A large group of these first generation seedlings, growing on their own root, were planted and maintained under close observation by us. In September of 1995, we removed a bud stock from the most vigorous seedlings and budded these to Citation Rootstock (U.S. Plant Pat. No. 5,112). It was from these budded trees that we recognized the outstanding fruit characteristics of the present variety and selected it for commercialization.

ASEXUAL REPRODUCTION OF THE VARIETY

Asexual reproduction of the new and distinct variety of interspecific tree was by budding to Citation Rootstock, as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The present new and distinct variety of interspecific Prunus tree [(Plum×Plum Nectarine)×(Peach×Plum Peach)] is of large size, vigorous, upright in growth and is a regular and productive bearer of large, firm, red flesh, clingstone fruit with very good flavor and eating quality. The fruit is further characterized by being relatively uniform in size throughout the tree, having good storage and shipping quality, with an attractive reddish brown skin color and having high soluble solids, 17.5° Brix. In comparison to the fruit of the Interspecific Tree Dapple Dandy (U.S. Plant Pat. No. 9,554), the flesh of the new variety is darker red in color, the fruit shape is slightly more elongated, the skin color is a deeper reddish brown color and is approximately 2 weeks earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked, (shipping ripe), and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color terminology (except those in common terms) in accordance with Reinhold Color Atlas by A. Kornerup and J. H. Wanscher.

Tree:

*Size.*—Large. Pruned to 10 to 12 feet in height and width primarily for economical harvesting of fruit.

*Vigor.*—Vigorous. Tree growth of 5 to 6 feet in height and 4 to 5 feet in width the first growing season.

*Growth.*—Upright growth habit. Heavy production tends to spread width of tree, usually pruned to vase shape.

*Productivity.*—Productive. Fruit set usually two or more times desired amount, thinning necessary.

*Bearer.*—Regular. Heavy fruit set 4 consecutive years. No alternate bearing observed.

*Form.*—Usually pruned to vase shape.

*Density.*—Medium dense. Pruning to open center of tree to vase shape which improves sunlight and air movement to the center of tree to enhance fruit color and growth of fruit bearing wood.

*Hardiness.*—Hardy in all stone fruit growing areas of California. Tree growing in Zone 9, winter chilling is approximately 750 hours at or below 45° F.

Trunk:

*Size.*—Medium to large. Average circumference 15 inches measured at 14 inches above ground on 5 year old tree.

*Texture.*—Medium shaggy, becomes rougher with age of tree.

*Color.*—Brown to dark brown (5-D-3) to (5-E-5). Varies with age of tree.

Branches:

*Size.*—Medium. Average circumference 7 inches measured 47 inches above ground. Crotch angle approximately 30°. Angle increases with heavy crop load.

*Surface texture.*—Smooth to medium rough, varies with age of growth.

*Lenticels.*—Average number 34 within a 4 square inch surface. Average length— 1/8 inch. Average width— 3/64 inch. Size increases with growth of branch. Color— Light brown to golden brown (5-C-6) to 5-D-7).

*Color.*—First years new growth, olive brown to yellowish brown (4-D-6) to (4-E-8). Mature growth, brown to dark brown (6-D-6) to (6-F-6), becomes darker with age of growth.

Leaves:

*Size.*—Large. Average length 3 inches. Average width 1 13/32 inches.

*Form.*—Elliptic.

*Apex.*—Cuspidate.

*Base.*—Cuneate.

*Margin.*—Doubly serrate.

*Thickness.*—Medium.

*Surface texture.*—Upper surface relatively smooth, slightly indented over leaf veins, glabrous. Lower surface relatively smooth, small ridges created by midrib and pinnate veining, pubescent, very short.

*Petiole.*—Average length— 47/64 inch. Average width— 3/64 inch. Color, upper surface— Nankeen yellow to brownish orange yellow (3-B-7) to (5-C-7). Lower surface— pale green to greenish white (30-A-2) to (30-A-4).

*Glands.*—Globose. Number varies from 0 to 3. Average number 2. Size— minute, 1/64 inch. Color— light orange to grayish orange (6-A-6) to (6-B-6). Located on base of leaf blade and upper portion of petiole.

*Color.*—Upper surface— green to dark green (29-F-5) to (29-F-7). Lower surface— grayish green to green (29-D-6) to (29-E-8). Varies with soil fertility and age of leaf.

Flower buds:

*Size.*—Medium. Average length— 3/8 inch. Average width— 15/64 inch, 4 days before bloom.

*Number of buds per spur.*—Average number 8. Number varies from 4 to 25, primarily with size and age of spur.

*Form.*—Plump, free, conical, becoming elongated as bud matures.

*Hardiness.*—Hardy with respect to California winters.

*Color.*—Lower 2/3 of petals— white (1-A-1). Upper 1/3 of petals— pale pink (11-A-3).

Flowers:

*Size.*—Medium. Average height— 1/2 inch. Average diameter— 23/32 inch.

*Number of flowers per bud.*—Average number 2, varies from 1 to 3.

*Petals.*—Shape— orbicular, smaller at point of attachment. Number— five, alternately positioned to sepals Surface of upper edge varies from smooth to slightly scalloped. Color varies from white (1-A-1) to very pale pink (11-A-3) near upper surface. Size— average length 3/8 inch. Average width 5/16 inch.

*Sepals.*—Number— five, alternately positioned to petals. Medium size, ovate shape, apex rounded. Average length 1/8 inch. Average width 1/8 inch at point of attachment. Color, upper surface— olive green to olive yellow (2-D-6) to (2-D-7). Lower surface— olive to olive gray (3-D-5) to (3-D-7). Color varies with age of flower. Both surfaces glabrous.

*Stamens.*—Number varies from 26 to 30, per flower. Average number 30. Average length 5/16 inch. Filament color— white (1-A-1). Anther color— light orange (6-A-5).

*Pollen.*—Present, self-sterile, pollenizer required. Color— maize yellow (4-A-6).

*Pistil.*—Normally one. Average length— 11/32 inch. Color— pale yellow green (30-A-3). Positioned slightly below the anthers. Surface— glabrous.

*Pedicel.*—Average length 25/64 inch. Average width 3/64 inch. Color— pastel green (30-A-4).

*Aroma.*—Slight.

*Blooming period.*—Date of First Bloom Feb. 28, 2000. Date of Petal Fall Mar. 7, 2000. Varies slightly with climatic conditions.

*Color.*—The base color of the flower is white (1-A-1) with upper ⅓ of the petals pale pink (11-A-2). Color fades to white with age.

Fruit:

*Maturity when described.*—Firm ripe (shipping ripe).

*Date of first picking.*—Jul. 1, 2000.

*Date of last picking.*—Jul. 9, 2000 Varies slightly with climatic conditions.

*Size.*—Large. Average diameter axially— 2¼ inches to 2½ inches. Average transversely in suture plane— 2⅜ inches to 2½ inches. Average weight— 142 grams. Average weight varies slightly with fertility of the soil, amount of thinning and climatic conditions.

*Form.*—Nearly globose, slightly elongated in suture plane.

*Suture.*—Shallow, extends from base to apex.

*Ventral surface.*—Nearly rounded.

*Apex.*—Rounded, some fruit slightly retuse.

*Base.*—Retuse.

*Cavity.*—Rounded to slightly elongated in suture plane. Average depth— ⅜ inch. Average breadth— ½ inch.

Flesh:

*Ripens.*—Relatively even, only slightly earlier along suture.

*Texture.*—Firm, meaty.

*Fibers.*—Few, small, tender.

*Aroma.*—Very slight.

*Amydgalin.*—Undetected.

*Eating quality.*—Very good.

*Flavor.*—Very good.

*Juice.*—Moderate to heavy, enhances flavor, good balance between acid and sugar.

*Brix.*—Average Brix— 17.5°, varies slightly with number of fruit per tree and climatic conditions.

*Color.*—Varies from Chinese rouge to lobster red (9-A-8) to (9-D-8). A lighter glow with rays of pale yellow orange (6-A-3) to pastel red (7-A-4) extending from pit cavity outward. Color deepens with maturity of fruit. Pit cavity varies from garnet red to deep ruby (12-C-8) to (12D-8).

Stem:

*Size.*—Average length— ½ inch. Average diameter— ⅛ inch.

*Color.*—Olive brown (4-E-4) to (4-E-7).

Skin:

*Thickness.*—Medium, tenacious to flesh.

*Texture.*—Medium.

*Bloom.*—Moderate amount.

*Tendency to crack.*—None.

*Color.*—Golden yellow to brownish yellow (4-B-7) to (4-C-7) ground color. Overspread with Venetian red to garnet red (8-D-8) to (9-D-8). Small, minute rounded areas of exposed ground cover giving a randomly spaced, speckled pattern.

Stone:

*Type.*—Clingstone.

*Size.*—Medium to large. Average length— 1⅛ inches. Average width— ¾ inch. Average thickness— 7/16 inch.

*Form.*—Ovoid.

*Base.*—Straight.

*Apex.*—Acuminate.

*Surface.*—Very lightly pitted throughout. Small, narrow ridges running from base toward apex extending from ⅓ to ½ the length of the stone. One small, narrow groove on each side of suture.

*Sides.*—Equal to unequal. One side of some stones extend further outward from center of suture plane.

*Ridges.*—Small, very narrow.

*Tendency to split.*—None.

*Color.*—Varies from tan to light brown when dry (4-B-4) to (4-B-5).

Use: Dessert. Market— local and long distance.

Keeping quality: Good, held firm in cold storage (38–42° F.) for 2 weeks without internal flesh breakdown or loss of eating quality.

Shipping quality: Good, picking and packing of fruit gave minimal bruising of flesh or skin scarring.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous upright growth, and being a productive and regular bearer of large, clingstone fruit with very good flavor and eating quality, the fruit is further characterized by having firm flesh with good storage and shipping quality and, in comparison to the fruit of the Interspecific Tree Dapple Dandy (U.S. Plant Pat. No. 9,554), it has a darker red, more attractive flesh color and is approximately 2 weeks earlier in maturity.

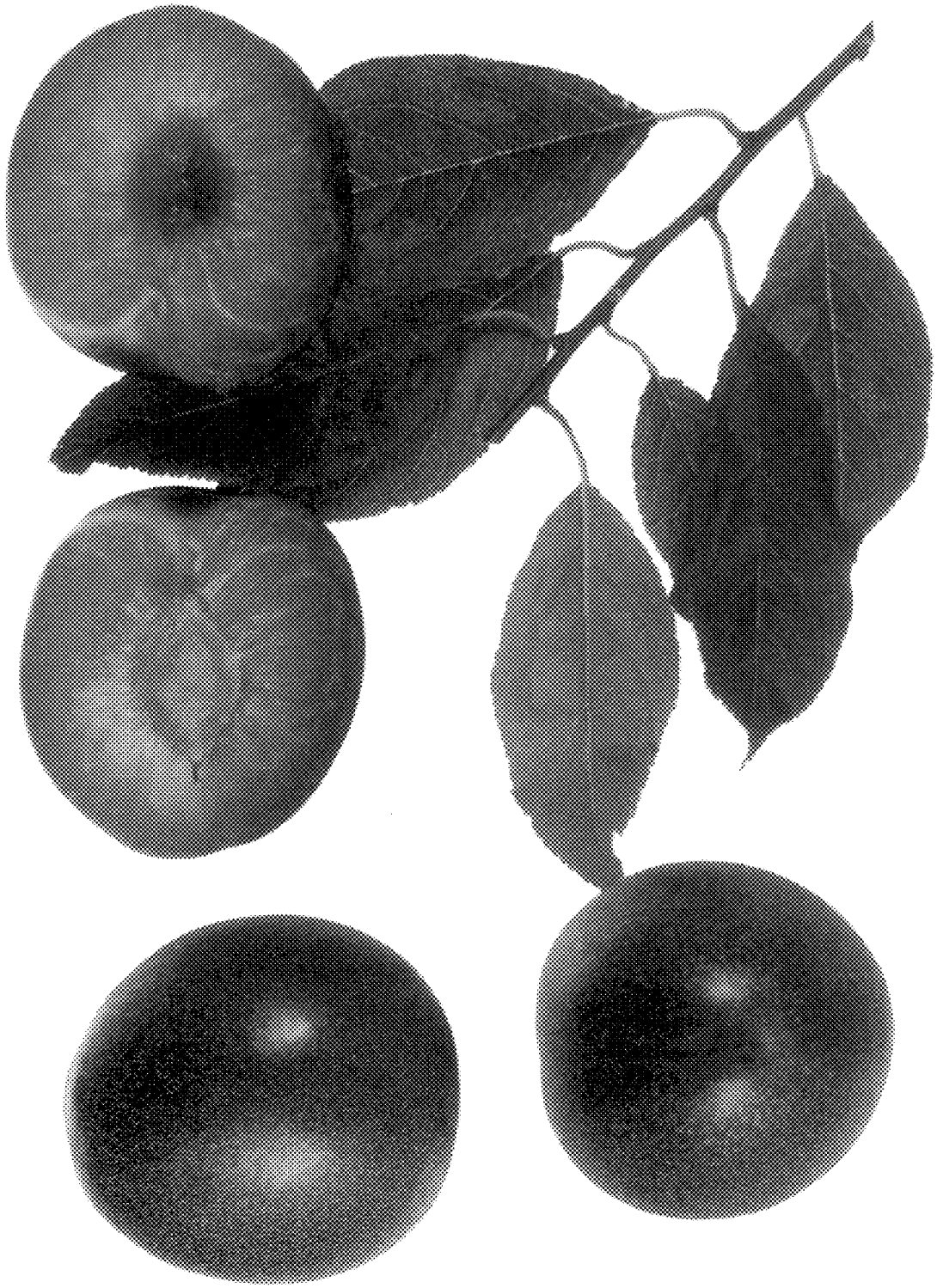

* * * * *